US007906969B2

(12) United States Patent  
Machida

(10) Patent No.: US 7,906,969 B2  
(45) Date of Patent: Mar. 15, 2011

(54) MAGNETIC RESONANCE DIAGNOSIS APPARATUS, NOISE SPATIAL DISTRIBUTION GENERATING METHOD, AND SIGNAL ACQUISITION METHOD

(75) Inventor: Yoshio Machida, Nasushiobara (JP)

(73) Assignees: Kabushiki Kaisha Toshiba, Minato-Ku, Tokyo (JP); Toshiba Medical Systems Corporation, Otawara-Shi, Tochigi (JP)

( * ) Notice: Subject to any disclaimer, the term of this patent is extended or adjusted under 35 U.S.C. 154(b) by 177 days.

(21) Appl. No.: 12/359,480

(22) Filed: Jan. 26, 2009

(65) Prior Publication Data

US 2009/0189606 A1     Jul. 30, 2009

(30) Foreign Application Priority Data

Jan. 28, 2008    (JP) ................................ 2008-016546

(51) Int. Cl.  
*G01V 3/00* (2006.01)

(52) U.S. Cl. ........................................ 324/318; 324/309

(58) Field of Classification Search .................. 324/318, 324/309  
See application file for complete search history.

(56) References Cited

U.S. PATENT DOCUMENTS

| 3,810,001 | A | * | 5/1974 | Ernst ............................ 324/313 |
| 5,297,033 | A | | 3/1994 | Bito et al. |
| 5,739,691 | A | * | 4/1998 | Hoenninger, III ............ 324/322 |
| 7,626,388 | B2 | * | 12/2009 | Taniguchi et al. ............ 324/309 |
| 2009/0096447 | A1 | * | 4/2009 | Prance et al. ................. 324/307 |

OTHER PUBLICATIONS

National Electrical Manufacturers Association: Determination of signal-to-noise ratio in diagnostic magnetic resonance imagers, NEMA Standard Publications, MS-1, 2001.  
Kasai and Doi, "MR Imaging Technology," Ohmsha, 2003.  
Ogura, et al., "Basic Study on Measurement of SNR of MR Image," Japanese Journal of Radiological Technology, 59(4), 508-513, 2003.  
Pruessmann KS, et al., SENSE: Sensitivity Encoding for Fast MRI, Magnetic Resonance in Medicine 42:952-962 (1999).  
Kellman P., et al., Image reconstruction in SNR units: A general method for SNR measurement, Magnetic Resonance in Medicine 54: 1439-1447 (2005).  
Reeder SB, et al., Practical Approaches to the evaluation of signal-to-noise ratio performance with parallel imaging: Application with cardiac imaging and a 32-channel cardiac coil, Magnetic Resonance in Medicine 54:748-754 (2005).  
Steckner MC, A new signal acquisition, two-image difference method for determining MR image SNR, Proc. Intl. Soc. Mag. Reson. Med. 1, p. 2398 (2006).  
Communication of Extended European Search Report dated Oct. 26, 2010 with attached European Search Report for EP 09000976.2-2209.

(Continued)

*Primary Examiner* — Brij B Shrivastav  
(74) *Attorney, Agent, or Firm* — Nixon & Vanderhye PC

(57) ABSTRACT

A magnetic resonance diagnosis apparatus includes a coil assembly including a high-frequency coil, a transmission unit which excites magnetization of a specific atomic nucleus of an object via the high-frequency coil, a reception unit including a detection unit for receiving a magnetic resonance signal via the high-frequency coil, a low-pass filter, and an analog/digital converter, a control unit which sets a passband of the low-pass filter to not less than three odd multiple of a frequency band determined from an imaging field of view, and sets a sampling frequency of the analog/digital converter to an oversampling frequency exceeding a signal band of the magnetic resonance signal, a noise spatial distribution generating unit which generates a noise spatial distribution on the basis of an output from the reception unit.

15 Claims, 12 Drawing Sheets

OTHER PUBLICATIONS

Mugler, J.P., et al., "Implementation of mixed bandwidth MRI pulse sequences using a single analog lowpass filter," Magnetic Resonance Imaging, Elsevier Science, Tarrytown, NY, US LNKD-DOI: 10.1016/0730-725X(89)90403-7, vol. 7, No. 5, Sep. 1, 1989, pp. 487-493, XP023256903, ISSN: 0730-725X.

Constantinides, C.D., et.al., "Signal-to-noise measurements in magnitude images from NMR phased arrays," Magnetic Resonance in Medicine, Academic Press, Duluth, MN, US LNKD-DOI: 10.1002/MRM.1910380524, vol. 38, No. 5, Nov. 1, 1997, pp. 852-857, XP007907123, ISSN: 0740-3194.

Dietrich, O., et al., "Measurement of signal-to-noise ratios in MR images: Influence of Multichannel coils, parallel imaging, and reconstruction filters," Journal of Magnetic Resonance Imaging, Society for Magnetic Resonance Imaging, Oak Brook, IL, US LNKD-DOI:10.1002/JMRI.20969, vol. 26, No. 2, Aug. 1, 2007, pp. 375-385, XP007915365, ISSN: 1053-1807.

Machida, Y., et al., "A Novel SNR Estimation Technique Applicable to Clinical Parallel MR Images: Triple Bandwidth," Proceedings of the International Society for Magnetic Resonance in Medicine, 16th Scientific Meeting and Exhibition, Toronto, Canada, May 3-9, 2008, vol. 16, Apr. 19, 2008, p. 3089, XP007915352.

* cited by examiner

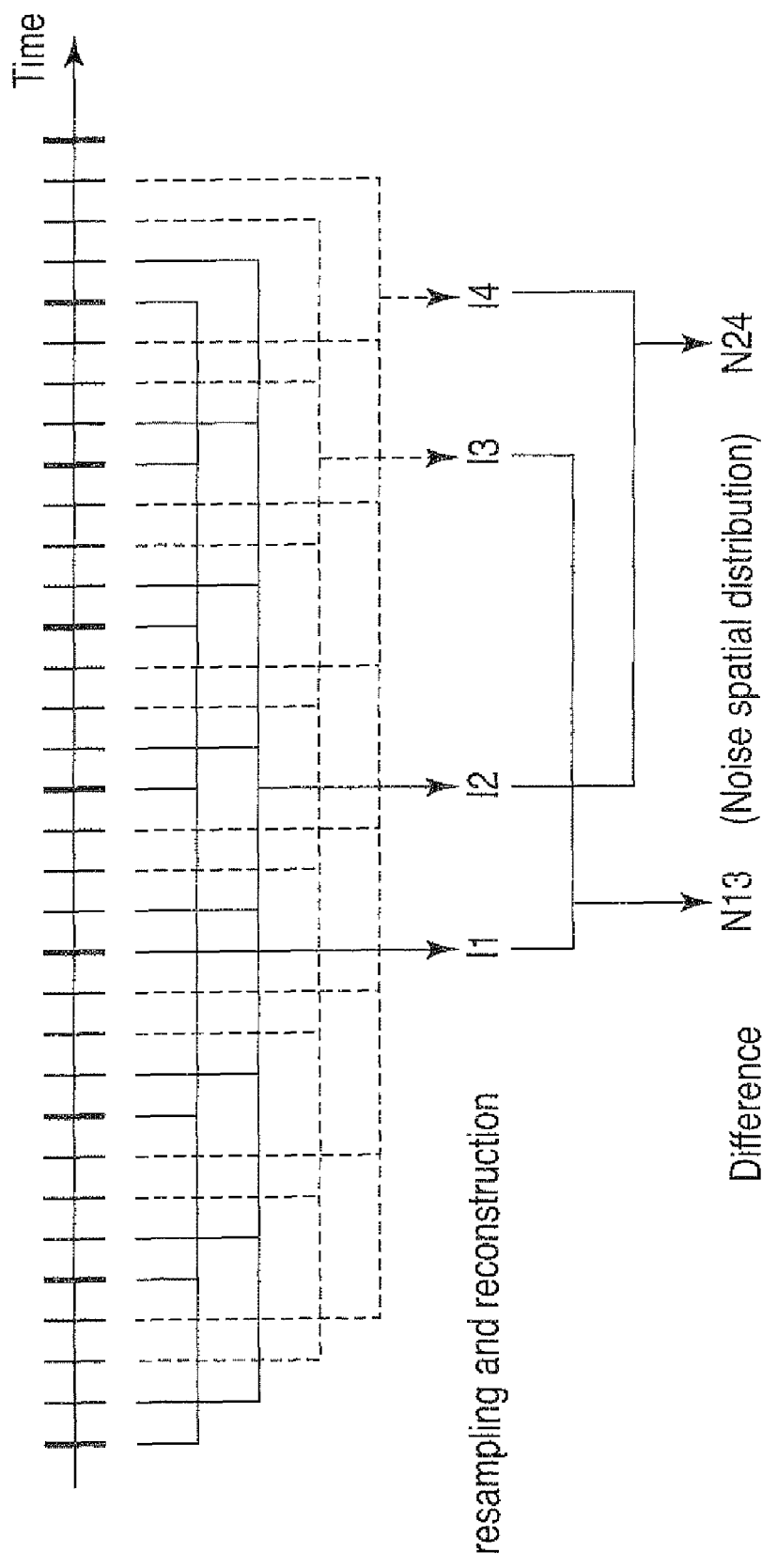
F I G. 9

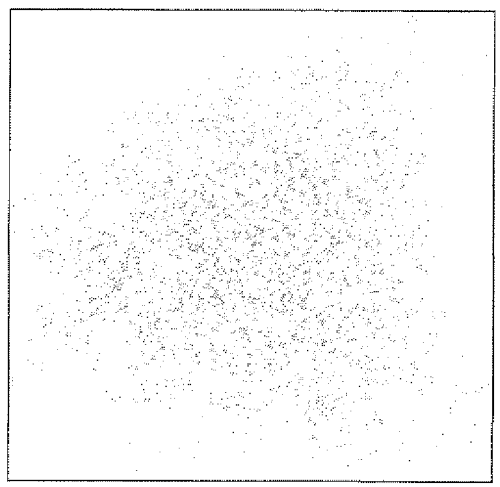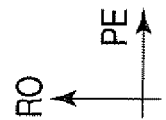
FIG. 10C
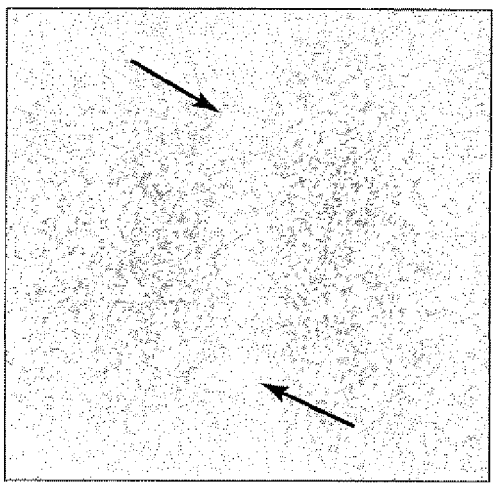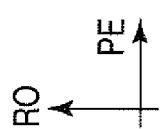
FIG. 10B
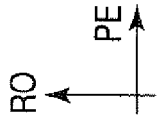
FIG. 10A

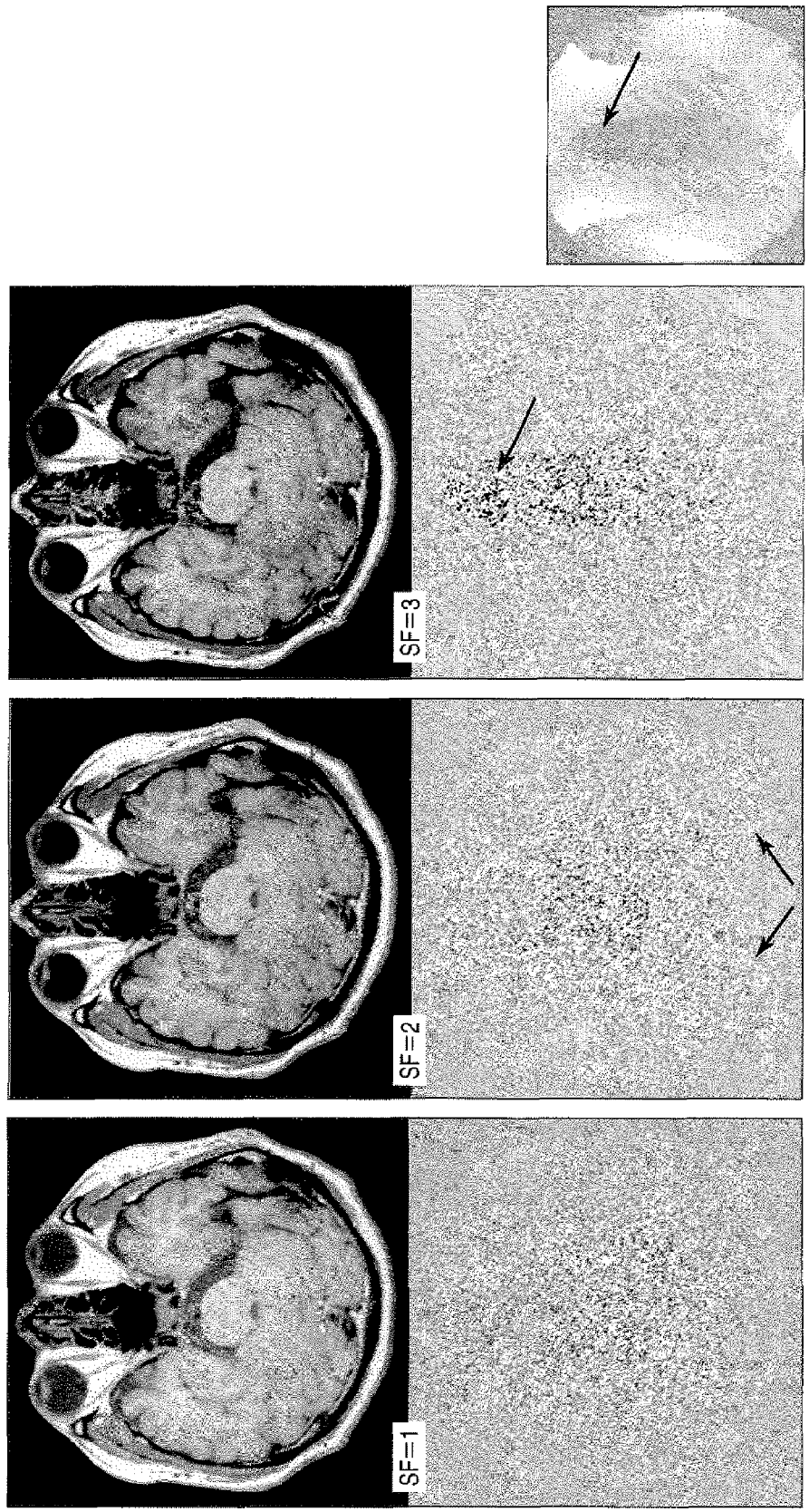

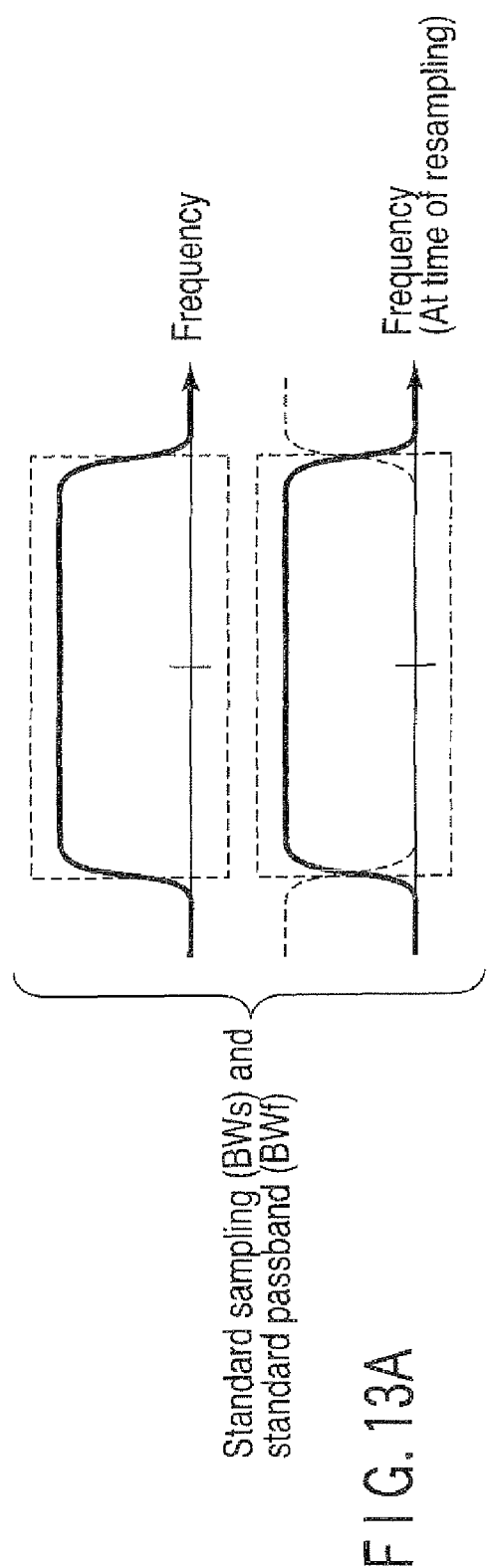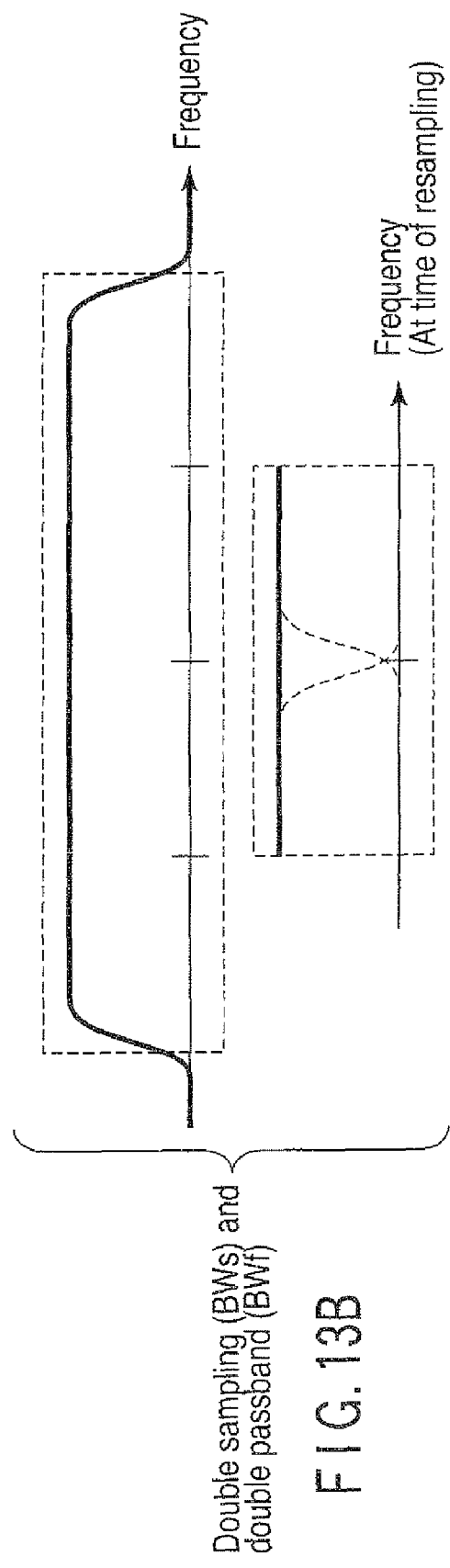

MAGNETIC RESONANCE DIAGNOSIS APPARATUS, NOISE SPATIAL DISTRIBUTION GENERATING METHOD, AND SIGNAL ACQUISITION METHOD

CROSS-REFERENCE TO RELATED APPLICATIONS

This application is based upon and claims the benefit of priority from prior Japanese Patent Application No. 2008-016546, filed Jan. 28, 2008, the entire contents of which are incorporated herein by reference.

BACKGROUND OF THE INVENTION

1. Field of the Invention

The present invention relates to a magnetic resonance diagnosis apparatus, a noise spatial distribution generating method, and a signal acquisition method.

2. Description of the Related Art

Several known methods are available to calculate the SNR (Signal-to-Noise Ratio) or CNR (Contrast-to-Noise Ratio) of an image. The following three methods can be given as typical methods in terms of measurement of noise components.

(1) Difference Method

The differences between the images captured under the same conditions are calculated, and reproducible components (containing Gibbs ringing in addition to signals) are removed from the differences, thereby extracting components corresponding to random noise. The SD (Standard Deviation) of the components is measured. This method is suitable when it is aimed at a phantom. A problem is, however, that it is difficult to repeatedly perform imaging under the same conditions when a person is imaged especially in a clinical case.

(2) Non-Difference Method: Measurement on Region of Interest without Difference Calculation (also Called "Same ROI Method" or the Like)

Signal components are required to be flat. However, MR images often contain low-order spatial components (gradual signal changes) due to various factors, and hence this requirement is difficult to meet. If a person is an object, the requirement is difficult more often to meet because of the inevitable existence of the original anatomical structure. In the case of a person, this problem is difficult to solve, and hence this method cannot be said to be a proper method.

(3) Non-Difference Method: Substitution by Background SD (Also Called "Spatial Noise Method" or the Like)

Although a signal component is measured in a region of interest ROI, a noise component is substituted by the standard deviation SD or average value of a background portion without any signal. A background portion of an absolute-value image has a different noise characteristic, a measured value in the background is converted into the noise amplitude of a signal portion. This method has been used most widely. No significant problems have arisen in the images obtained by a single coil and the sum-of-square method (SOS method, more precisely, the Square Root of Sum-of-Square method) which is a typical image forming method using an array coil.

For example, a background portion B is assumed as a noise spatial distribution, and its standard deviation $\sigma(B)$ is obtained. Obtaining signal portion conversion value $\sigma'=\sigma'(B)$ which changes depending on the number of channels of the array coil from the standard deviation $\sigma(B)$ can obtain noise representing this image. The SNR of a parenchymal organ 1 can be obtained by dividing an average value $m(O1)$ of an observation signal in a local region by the value $\sigma'$ described above, i.e., can be given by $m(O1)/\sigma'$. Likewise, the CNR between the parenchymal organ 1 and a parenchymal organ 2 is calculated as $(m(O1)-m(O2))/\sigma'$. Clinically, the CNR of a parenchymal organ adjacent to a morbid region L is represented by $(m(L)-m(O1))/\sigma'$.

Each technique described above is based on the assumption that the noise intensity in an image is relatively invariable, i.e., uniform. If, therefore, the noise intensity in an image is relatively variable depending on positions in the image, the reliability of conventional noise evaluation deteriorates. For example, with recent advances in parallel imaging (PI) in MRI, noise has not become spatially uniform due to sensitivity irregularity correction processing for a surface array coil used for PI and PI unfolding processing.

In consideration of these situations, evaluation methods have recently been proposed. Reference 5 described below discloses a method of evaluating an SNR at each point of a final image by using added pre-scan data. This method is a strict method but uses information other than a generally obtained final image, and hence cannot be directly used at a clinical site.

On the other hand, as a more practical approach, there is proposed a method of obtaining the SNR or CNR of a final image obtained in inspection by estimating a noise component from the image alone. This is important in terms of clinical inspection or clinical research. Another proposed method is a method of regarding a curved surface approximated in a designated ROI as a proper signal component and using a difference from it as source data for distributed calculation. However, this method has a problem that it is difficult to set an ROI due to an anatomical structure or that if an ROI is set in accordance with an anatomical structure, since the ROI becomes small, the accuracy of distributed estimation deteriorates in statistical terms.

In addition to the above methods, there is available a method which basically calculates a standard deviation SD at each point by using many images captured continuously. This method is obviously premised on temporal reproducibility but can be a most acceptable noise component estimation method at each point. The use of this method is reported in the following reference. However, the method requires continuous imaging, and hence is designed for evaluation limited to part of fast imaging.

A method based on oversampling in read operation has recently been proposed by Steckner. This method is not easily influenced by the movement of an object. However, the cutoff characteristic of a low-pass filter (LPF) sometimes comes into play in the center of an image. If importance is placed on the in-plane distribution of SNRs, therefore, a more reliable method is required.

In general, it is difficult to calculate the SNR or noise index of a recent MRI image containing non-uniform noise components. It is conventionally impossible to perform such calculation in imaging operation for a person whose movement influences the operation without fail. Although there are strong demands for a practical noise spatial distribution calculation method, there is no such method available.

Reference 1: National Electrical Manufacturers Association: Determination of signal-to-noise ratio in diagnostic magnetic resonance imagers, NEMA Standard Publications, MS-1, 2001

Reference 2: Kasai and Doi, "MR Imaging Technology", Ohmsha, 2003

Reference 3: Ogura, et al., "Basic Study on Measurement of SNR of MR Image", Japanese Journal of Radiological Technology, 59(4), 508-513, 2003

Reference 4: Pruessmann K S, et al., SENSE: Sensitivity Encoding for Fast MRI, Magnetic Resonance in Medicine 42: 952-962 (1999)

Reference 5: Kellman P, et al., Image reconstruction in SNR units: A general method for SNR measurement, Magnetic Resonance in Medicine 54: 1439-1447 (2005)

Reference 6: Reeder S B, et al., Practical Approaches to the evaluation of signal-to-noise ratio performance with parallel imaging: Application with cardiac imaging and a 32-channel cardiac coil, Magnetic Resonance in Medicine 54: 748-754 (2005)

Reference 7: Steckner M C, A new signal acquisition, two-image difference method for determining MR image SNR, Proc. Intl. Soc. Mag. Reson. Med. 14(2006), p. 2398

BRIEF SUMMARY OF THE INVENTION

It is an object of the present invention to generate a high-accuracy noise spatial distribution even in a situation in which noise components vary with time, and the influence of the movement of a person as a target cannot be ignored.

According to an aspect of the present invention, there is provided a magnetic resonance diagnosis apparatus comprising: a coil assembly including a high-frequency coil; a transmission unit which excites magnetization of a specific atomic nucleus of an object by driving the high-frequency coil; a reception unit including a detection unit which receives a magnetic resonance signal via the high-frequency coil, a low-pass filter, and an analog/digital converter; a control unit which sets a passband of the low-pass filter to not less than three odd multiple of a frequency band determined from an imaging field of view, and sets a sampling frequency of the analog/digital converter to an oversampling frequency exceeding a signal band of the magnetic resonance signal; and a noise spatial distribution generating unit which generates a noise spatial distribution on the basis of an output from the reception unit.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 9 is a view showing four resampled data sets corresponding to quadruple oversampling, reconstructed images corresponding to the respective data sets, and a noise spatial distribution (difference image) in this embodiment;

FIG. 10A is a view showing a reconstructed image;

FIG. 10B is a view showing a conventional noise spatial distribution;

FIG. 10C is a view showing a noise spatial distribution in this embodiment;

FIG. 11A is a view showing a reconstructed image with speed factor SF=1, which is obtained by parallel imaging, and its noise spatial distribution in this embodiment;

FIG. 11B is a view showing a reconstructed image with speed factor SF=2, which is obtained by parallel imaging, and its noise spatial distribution in this embodiment;

FIG. 11C is a view showing a reconstructed image with speed factor SF=3, which is obtained by parallel imaging, and its noise spatial distribution in this embodiment;

FIG. 11D is a view showing a g-factor noise spatial distribution in this embodiment;

FIG. 13A is a view showing standard imaging conditions; and

FIG. 13B is a view showing a noise aliasing characteristic at the time of resampling in the prior art.

DETAILED DESCRIPTION OF THE INVENTION

An embodiment of the present invention will be described with reference to the views of the accompanying drawing. The related art will be described before the description of this embodiment.

1) MRI Data Acquisition Conditions (Read Direction)

In MRI data acquisition, a reading gradient magnetic field strength, the number of data sampling points, a data sampling rate (pitch), and the like are determined from imaging conditions (an imaging field of view FOV, the number of matrices, phase nowrap designation, and the like). Data is filtered by analog low-pass filter $BW=BW_{13}$ lpf corresponding to band BWs=BW_smpl. Although a digital filter is normally used, equivalent processing is performed when data is generated from original high-rate sampled data. The following discussion is premised on two bands, i.e., sampling band BWs=BW_smpl and analog filter band BWf=BW_lpf in either case. Assume that the term "band" generally indicates the latter, i.e., BWf=BW_lpf.

Most standard conditions are determined from an FOV and the number of matrices, and are conditions without phase nowrap (without oversampling). Assume that they are standard imaging conditions. For example, FOV=20 cm, sampling pitch=24 µs, and (gradient magnetic field strength=4.9 mT/m (2.1 kHz/cm)) are standard conditions. Note that BWf=BWs=41.7 kHz (FIG. 13A). Although it is conceivable that oversampling is internally and automatically performed in the read direction, the following description in this specification will be made on the assumption that data has been acquired as designated.

2) Single Acquisition, Two-Image Difference Method (Prior Art)

Conventionally, in the single acquisition, two-image difference method, double oversampling is performed in the read direction, and data are reconstructed upon alternately dividing the double number of acquisition points into two groups. That is, one image Iodd (=I1) is obtained from odd-numbered data, and the other image Ieven (=I2) is obtained from the other even-numbered data. Double BWf and double BWs are set in a standard oversampling mode. According to the Fourier transform shift theorem, the two images are shifted from each other by one sampling position in the read direction (time direction), and hence phase distortion occurs on the images in the read direction accordingly. These images are totally identical in terms of absolute values. On the other hand, noise components are independent of each other. Since a drift in the apparatus which is caused by a time difference corresponding to one sampling point can be generally ignored, calculating difference N=I1−I2 between the two images can completely remove original signal components and can obtain only a noise image.

FIG. 13B shows an aliasing state in this method. The singularity of an original cutoff frequency component is folded to the central portion.

Figure 1:
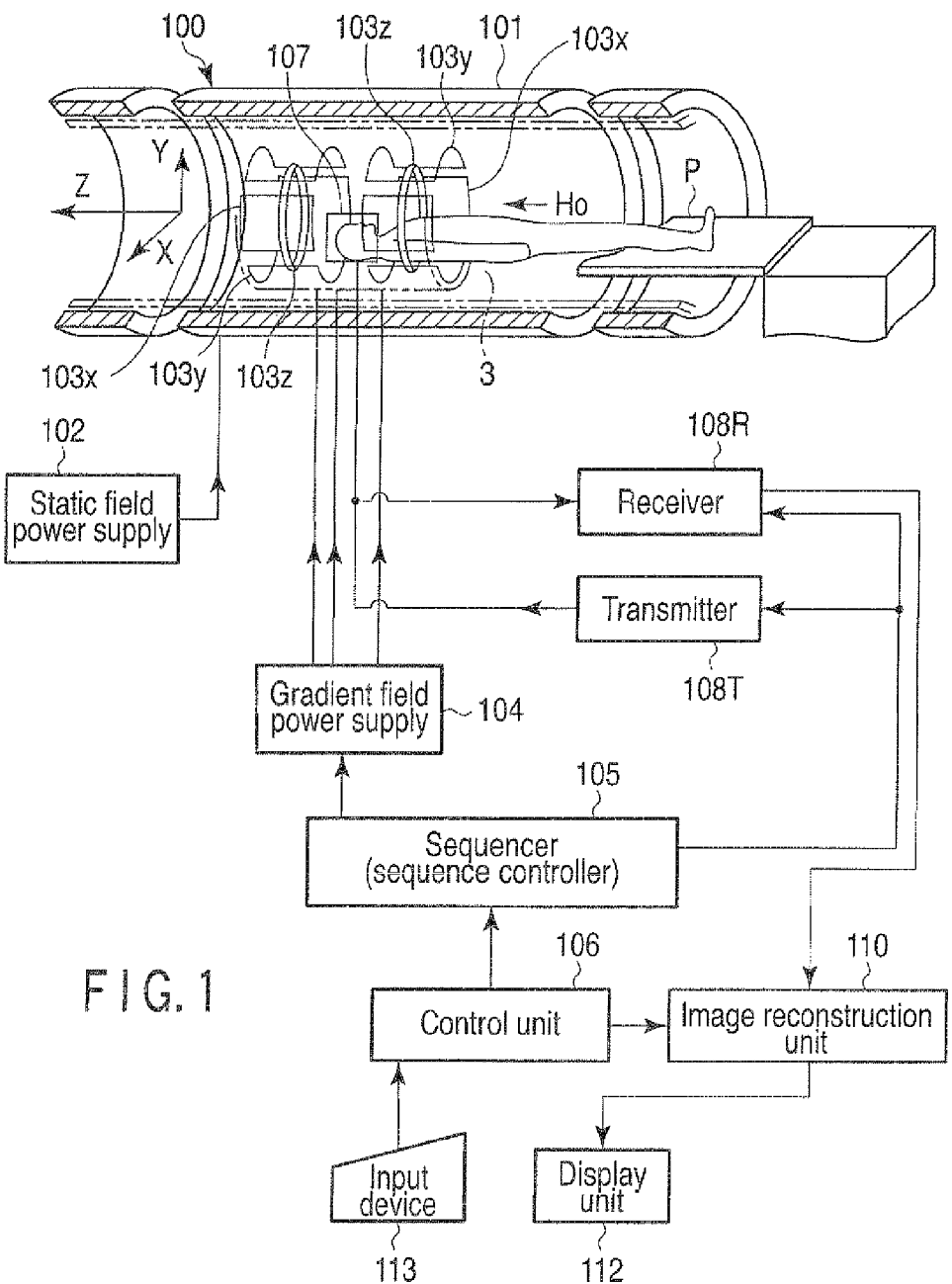
FIG. 1 is a view showing the arrangement of a magnetic resonance diagnosis apparatus according to an embodiment.

This embodiment will be described below. As shown in FIG. 1, the magnetic resonance diagnosis apparatus (MRI apparatus) according to an embodiment includes a coil assembly 100 as a main structure. A nearly cylindrical opening portion is formed in an almost middle portion of the coil assembly 100. At the time of imaging, an object is inserted into the opening portion while being placed on a bed. For the sake of convenience, three orthogonal axes X, Y, and Z are defined with the center of this opening portion being the origin. Assume that a Z-axis is defined in a direction parallel to the axial direction of the opening portion.

The coil assembly 100 is provided with a high-frequency coil (RF coil) 107, gradient field coil sets 103x, 103y, and 103z, a static field coil 101 which are sequentially arranged around the opening portion from the inner side. Upon receiving a current from a static field power supply 102, the static field coil 101 generates a uniform static field in an imaging region in the opening portion. The gradient field coil sets 103x, 103y, and 103z respectively correspond to the three axes X, Y, and Z. These three coils individually receive currents from a gradient field power supply 104, and superimposes gradient fields whose field strengths are inclined along the X-, Y-, and Z-axes on the static field.

The gradient fields along the X-, Y-, and Z-axes are made to respectively correspond to a slice selection gradient field Gs for determining, for example, an arbitrary imaging slice, a phase encoding gradient field Ge for encoding the phase of a magnetic resonance signal in accordance with a spatial position, and a readout gradient field Gr for encoding the frequency of a magnetic resonance signal in accordance with a spatial position.

The high-frequency coil 107 receives, from a transmitter 108T, a high-frequency current pulse whose frequency is adjusted, and generates a high-frequency magnetic pulse. When the pulse length of this high-frequency magnetic field pulse is relatively short, the magnetization spin of a specific atomic nucleus in the object is excited to generate a transverse magnetization component. When the pulse length of a high-frequency magnetic field pulse is relatively long, the phase lag/lead of the magnetization spin is inverted. The former high-frequency magnetic field pulse is a so-called exciting pulse, and the latter is called an inverting pulse (refocus pulse).

The transmitter 108T includes an oscillation unit which generates a high-frequency signal having a resonance frequency unique to a target atomic nucleus in a static field, a phase selecting unit which selects the phase of a high-frequency signal, a frequency modulation unit which modulates the frequency of a phase-selected high-frequency signal, an amplitude modulation unit which modulates the amplitude of a frequency-modulated high-frequency signal in accordance with the sinc function, and a high-frequency power amplification unit which amplifies the amplitude-modulated high-frequency signal and supplies it the high-frequency coil 107.

Figure 2:
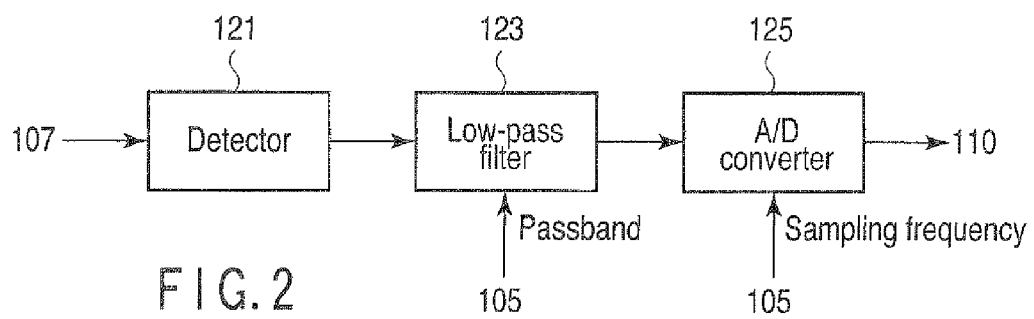
FIG. 2 is a block diagram showing the arrangement of a receiver in FIG. 1.

A receiver 108R receives the magnetic resonance signal generated from the transverse magnetization component of a magnetization spin via the high-frequency coil 107. As shown in FIG. 2, the receiver 108R detects the phase of a received magnetic resonance signal by using a detector 121, and converts the signal into a digital signal by using an analog/digital converter 125 via a low-pass filter 123.

A control unit 106 controls the gradient field power supply 104, the transmitter 108T, and the receiver 108R to execute a predetermined pulse sequence. The passband of the low-pass filter 123 of the receiver 108R and the sampling frequency of the analog/digital converter 125 are, in particular, variable. The control unit 106 arbitrarily sets a passband and a sampling frequency.

Although described in detail later, the control unit 106 sets the passband of the low-pass filter 123 to about a three or more odd multiple of the frequency band (standard passband) determined from an imaging field of view, and also sets the sampling frequency of the analog/digital converter 125 to an oversampling frequency exceeding the frequency corresponding to the signal band of a magnetic resonance signal. An input device 113 is connected to the control unit 106. The operator designates, via the input device 113, how many times of the frequency band determined from an imaging field of view the passband of the low-pass filter 123 is set, and can designate how many times of the signal band the sampling frequency of the analog/digital converter 125 is set.

An image generating unit 110 mainly functions to reconstruct image data from the data output from the receiver 108R by performing Fourier transform along the phase encoding axis and the frequency encoding axis.

The image generating unit 110 also resamples (subsamples) the data output from the receiver 108R and returns the frequency to a sampling frequency corresponding to the signal band of magnetic resonance signals, thereby generating a plurality of resampled data sets which differ in sampling position. The image generating unit 110 reconstructs a plurality of images on the basis of the plurality of resampled data sets. When double oversampling is set, two resampled data sets which differ in resampling position are generated. Two images are reconstructed on the basis of the two resampled data sets, respectively. When triple oversampling is set, three resampled data sets which differ in resampling position are generated. Three images are reconstructed on the basis of the three resampled data sets, respectively. When quadruple oversampling is set, four resampled data sets which differ in resampling position are generated. Four images are reconstructed on the basis of the four resampled data sets, respectively.

The image generating unit 110 reconstructs a plurality of images which differ in resampling point, and generates a noise spatial distribution by calculating the differences between the plurality of images. A display unit 112 is provided for the main purpose of displaying the images and noise spatial distributions generated by the image generating unit 110.

Setting of the passband of the low-pass filter 123 and the sampling frequency of the analog/digital converter 125 will be described below.

Figure 3:
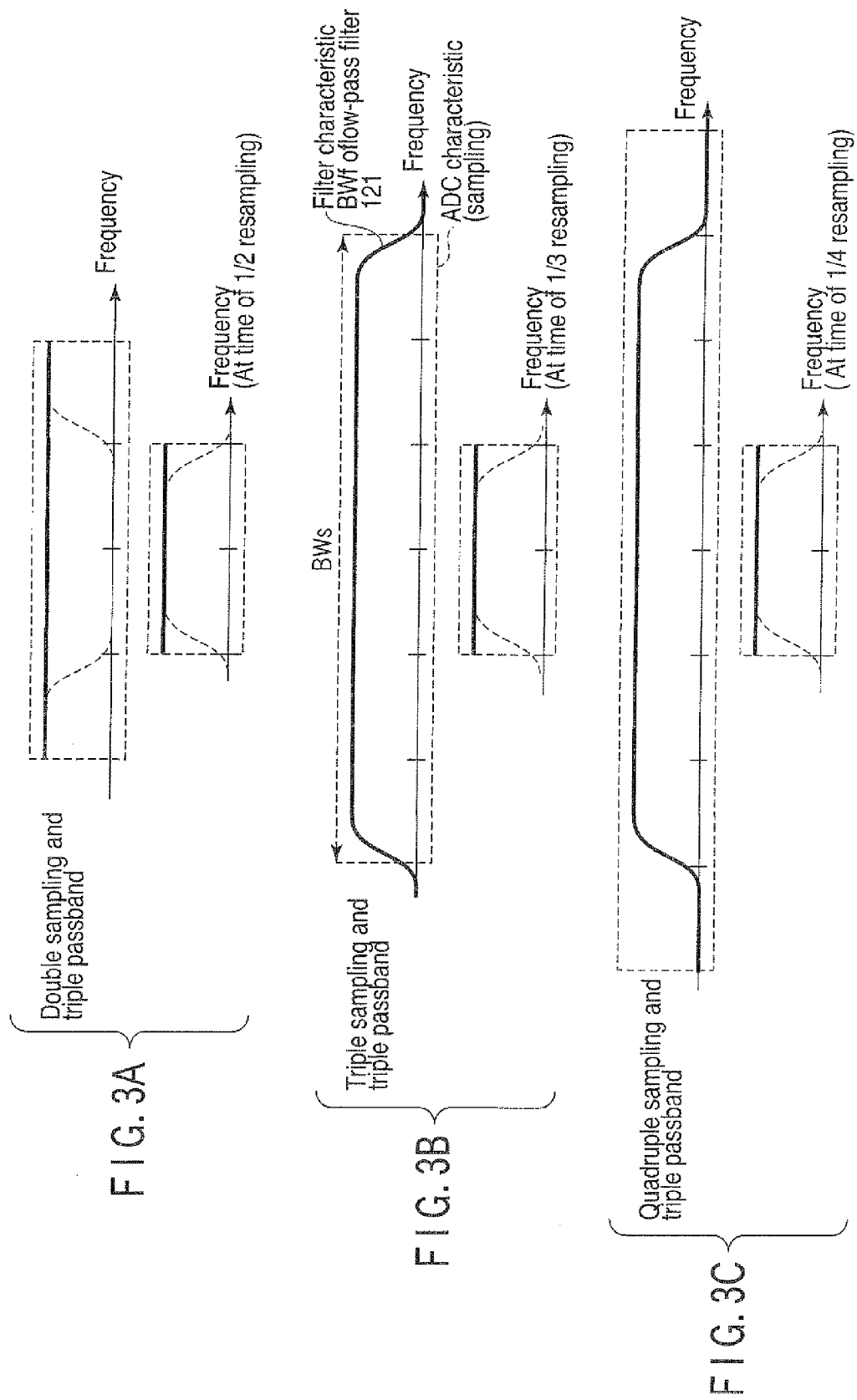
FIG. 3A is a view showing double-frequency sampling and a triple passband in this embodiment in comparison with resampling.
FIG. 3B is a view showing triple-frequency sampling and a triple passband in this embodiment in comparison with resampling.
FIG. 3C is a view showing quadruple-frequency sampling and a triple passband in this embodiment in comparison with resampling.

In this embodiment, if n is set to an odd number of three or more and the passband is widened to n·BWf, an oversampling band is given by ((n+1)/2)·BWs with respect to the signal band BWs. For example, as shown in FIG. 3A, double oversampling is set in a triple band. Alternatively, triple oversampling is set in a quintuple band.

For precise image quality evaluation, the prior art has a problem in that a noise characteristic near the center of an image reconstructed from sub-sampled data is abnormal, as described above. In this embodiment, therefore, the passband BWf of the low-pass filter 123 for noise measurement is set to about triple the frequency band determined from an imaging field of view (see FIGS. 3A, 3B, and 3C). This setting triples aliasing when an image is reconstructed from resampled (sub-sampled) data. As a consequence, abnormal portions of the characteristic are located at the two ends of the desired imaging field of view FOV. Although the cutoff characteristic of the low-pass filter 123 is blunted because the passband is extended by three times, a flat characteristic is maintained in the central portion of the image which is most important. Therefore, the noise image obtained by the difference image becomes a noise characteristic itself which is generated from signal reception by image generation processing.

Figure 4:
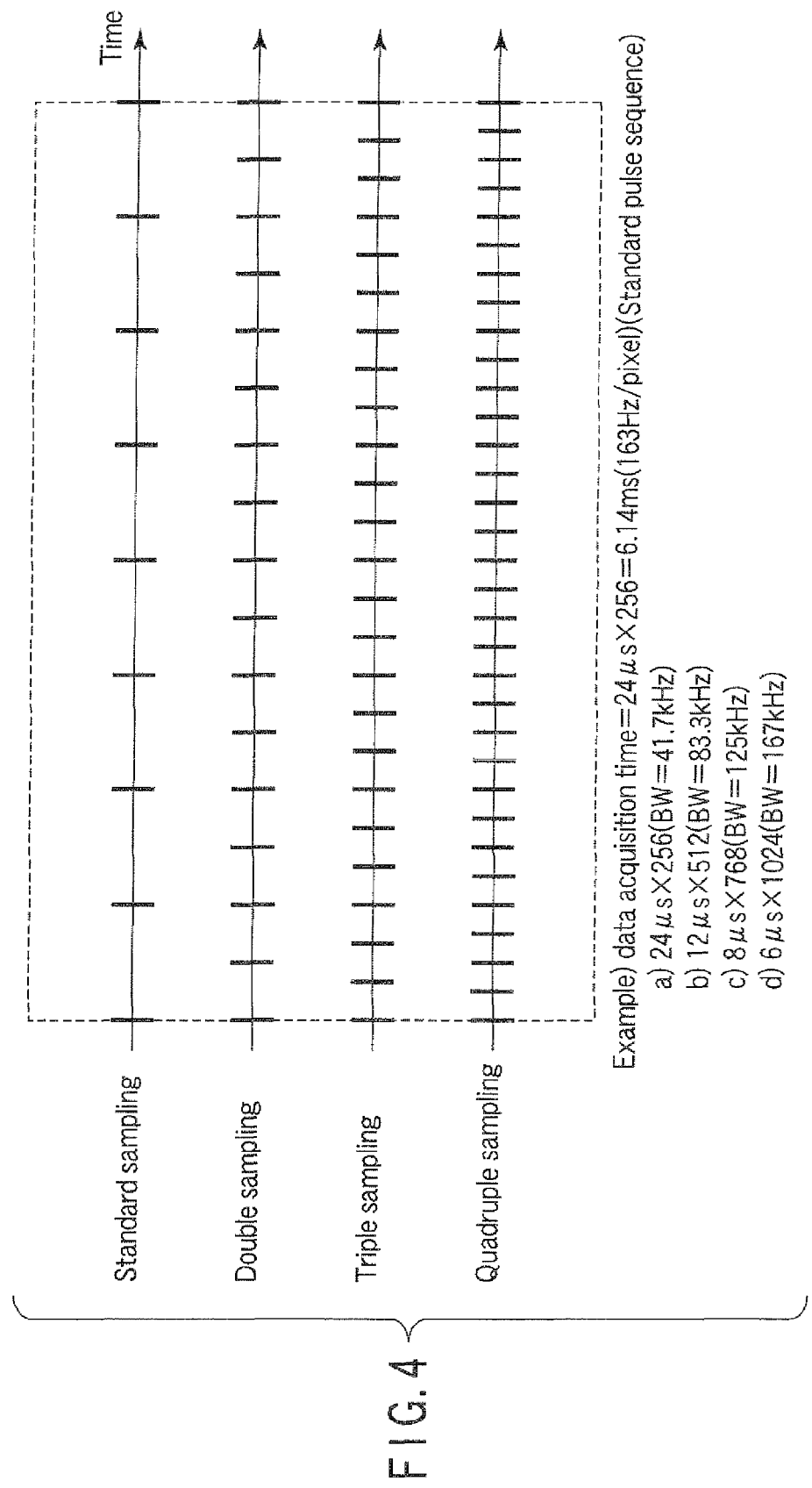
FIG. 4 is a view showing sampling points in oversampling in this embodiment.

The band BWs determined from the sampling frequency of the analog/digital converter (ADC) 125 by the Nyquist theorem is normally matched with the passband WBf of the low-pass filter 123. FIG. 4 shows this state. The expression of sampling along the time axis corresponds to FIG. 4. In practice, sampling can be double sampling in FIG. 4 (corresponding to FIG. 3A) or quadruple sample in FIG. 4 (corresponding to FIG. 3C).

Figure 5:
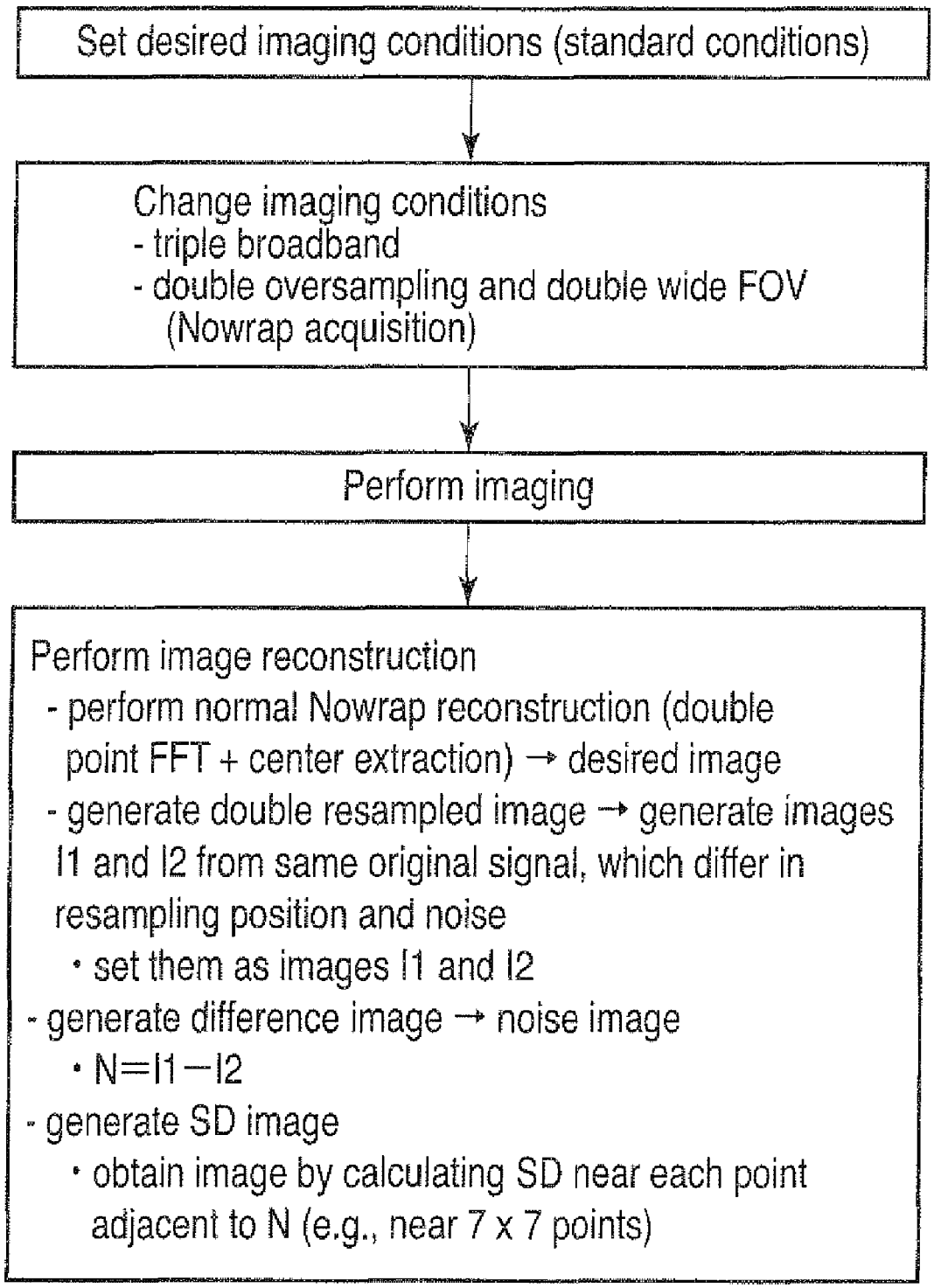
FIG. 5 is a flowchart showing a sequence for generating a noise spatial distribution at the time of double oversampling in this embodiment.
Figure 6:
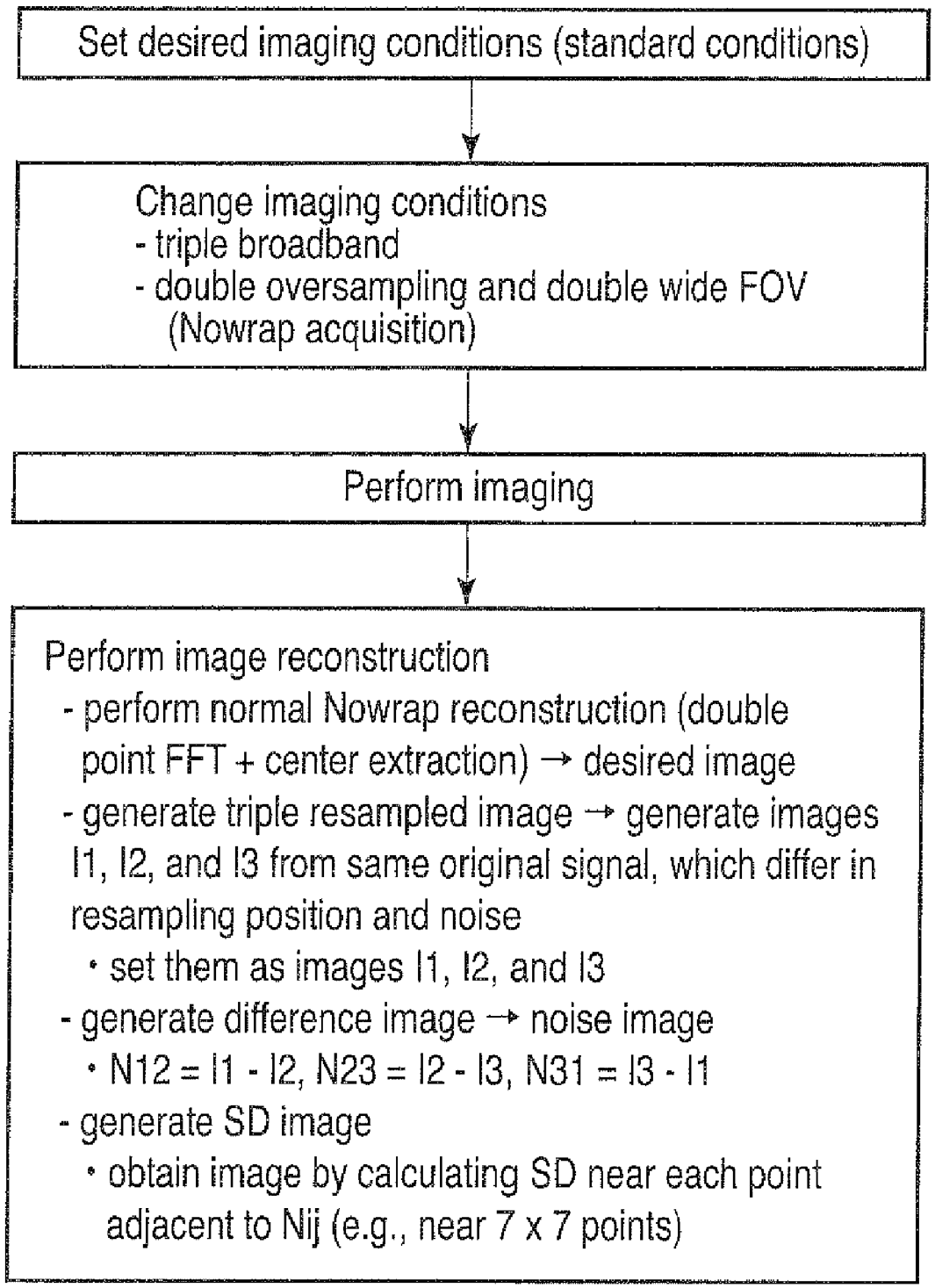
FIG. 6 is a flowchart showing a sequence for generating a noise spatial distribution at the time of triple oversampling in this embodiment.
Figure 7:
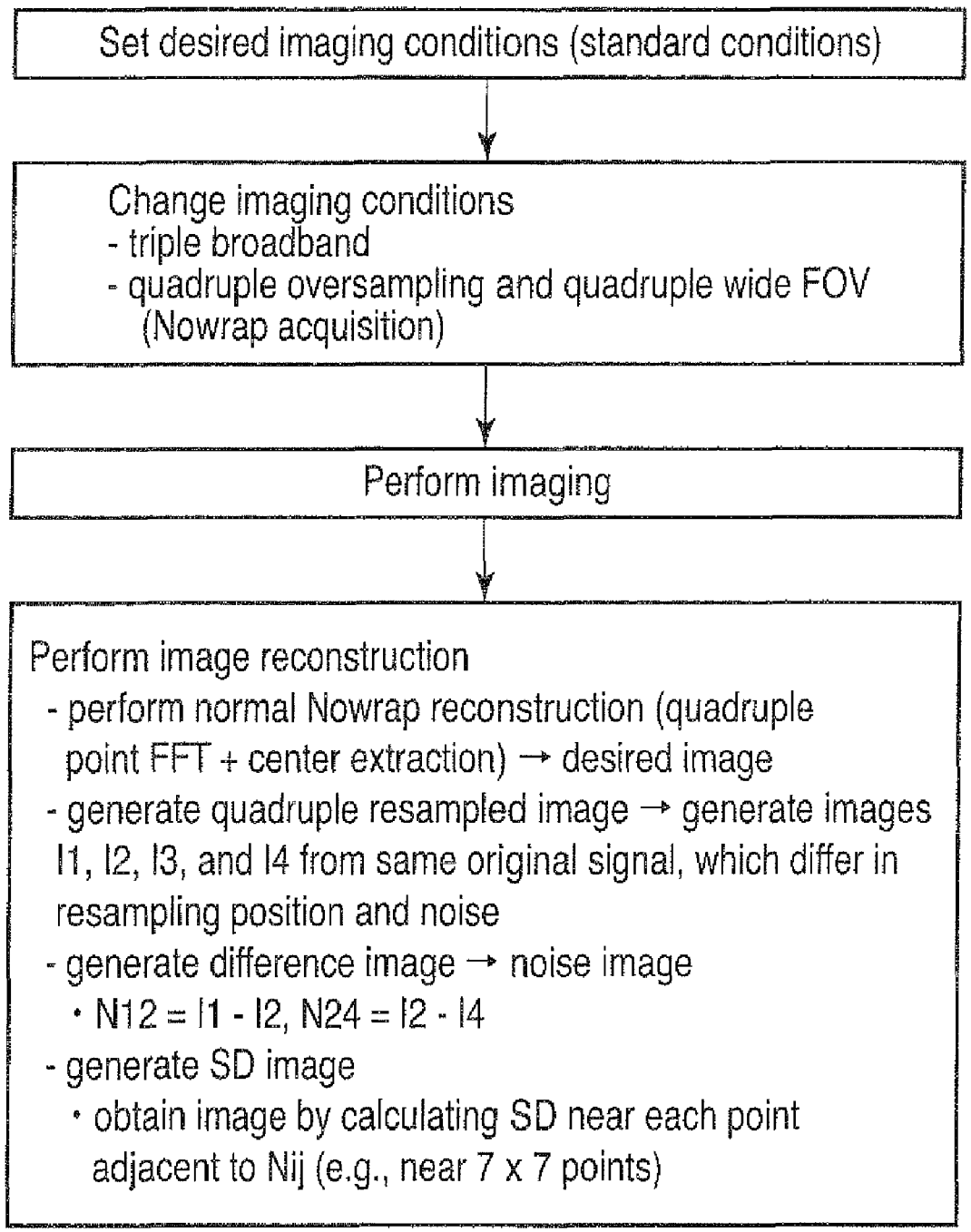
FIG. 7 is a flowchart showing a sequence for generating a noise spatial distribution at the time of quadruple oversampling in this embodiment.
Figure 8:
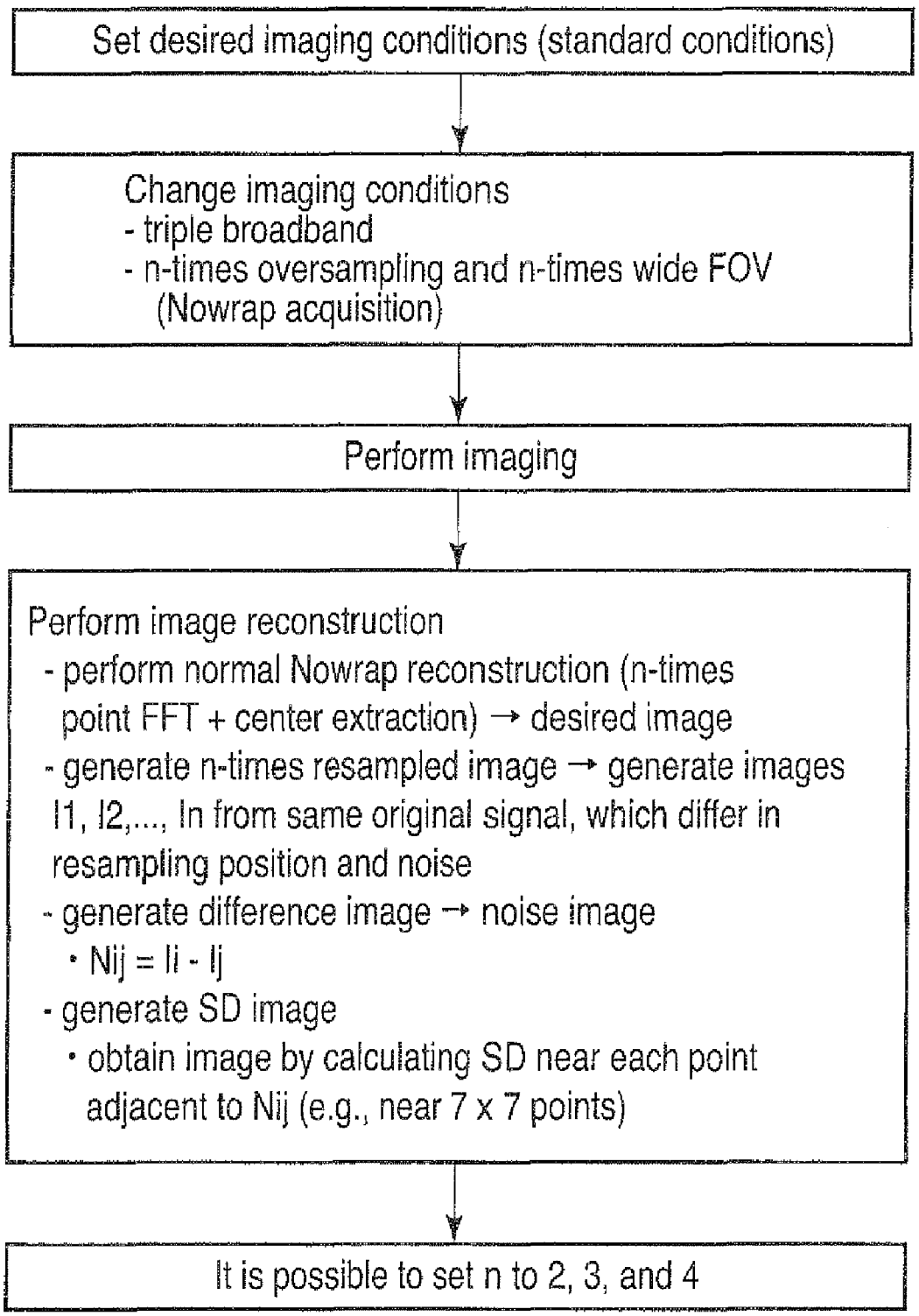
FIG. 8 is a flowchart showing a sequence for generating a noise spatial distribution at the time of n-times oversampling in this embodiment.
Figure 12:
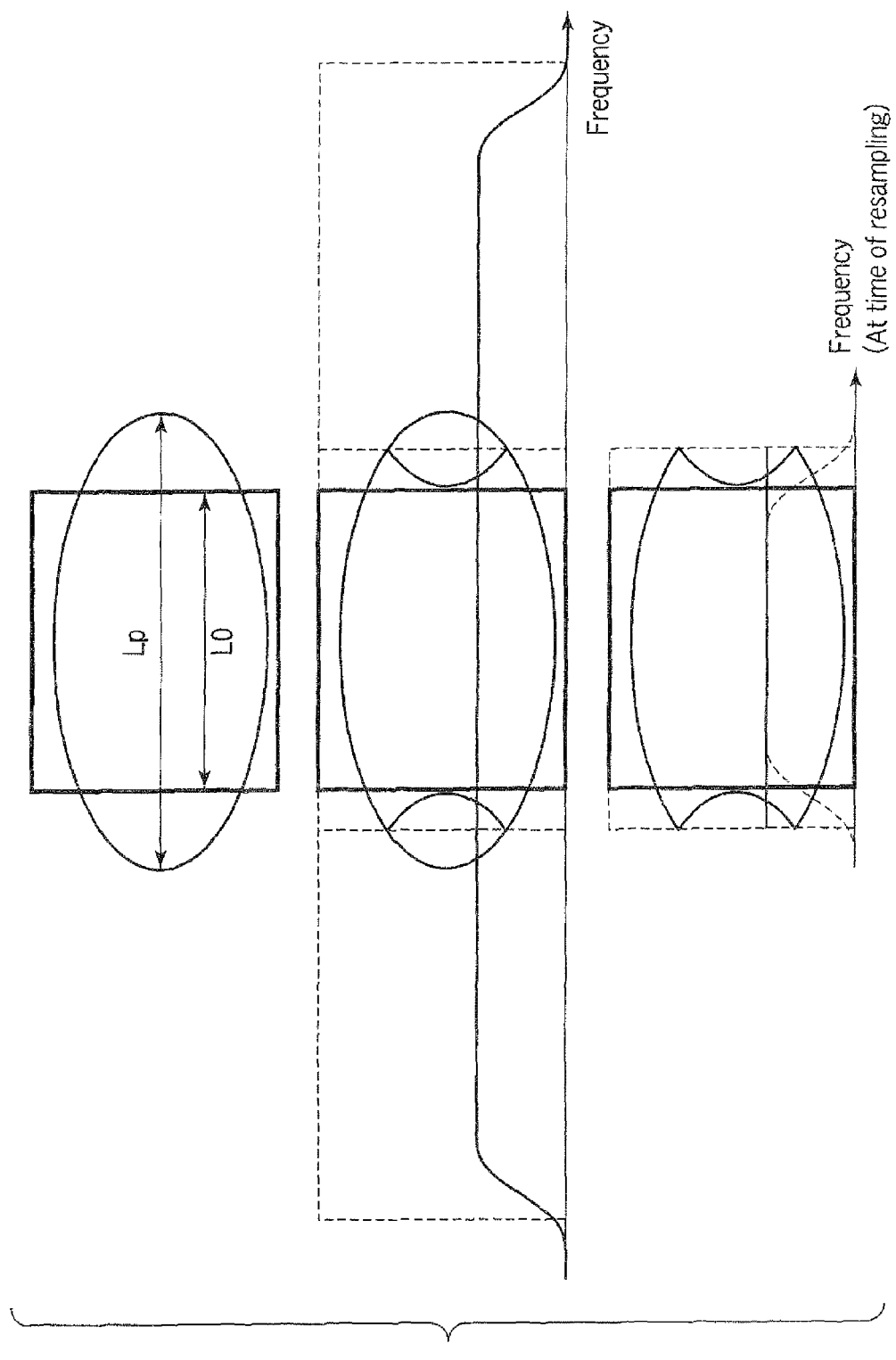
FIG. 12 is a view showing an example in which this embodiment also uses a technique of preventing aliasing with respect to an object.

FIGS. 5, 6, and 7 are flowcharts respectively showing cases in which the band BWs of the analog/digital converter 125 is set to double, triple, and quadruple the signal hand with the passband WBf of the low-pass filter 123 being fixed to triple the standard band. FIG. 8 provides a summary of the sequences. FIG. 9 shows how data are handled in the case of quadruple BWs.

The case of triple BWf and double BWs is equivalent to the case in which only images I1 and I3 (or only images I2 and I4) generated by triple WBf and quadruple BWs are observed in practice. Therefore, there is no shortage of the number of points, and two data with sufficiently high noise independency can be obtained. That is, the setting of triple BWf and double BWs is more practical than the setting of triole BSf and triple BWs, which is natural setting, in terms of the generation of a noise map. In the fast imaging method with a high sampling rate, a limitation is sometimes imposed on oversampling. In this case, the setting of triple BWf and double BWs is high in utility.

A concrete experimental example will be described next.
<Method>

An experiment was conducted by using a 1.5-tesla MRI apparatus. First of all, the experiment was executed by a whole-body coil using a homogenous phantom. The noise (standard deviation) of the noise spatial distribution in this embodiment was compared with the noise of a general image.

In the experiment, a five-channel head coil was used. The parameters set in the experiment were: the spin echo method (TR: 500 msec, TE: 15 msec), a 256×256 matrix (256 acquisition steps), the imaging field of view FOV: 20×20 cm, NEX: 2, a slice thickness: 5 mm, sensitivity correction, and no postprocessing filter. The following images were acquired for noise evaluation:

A) standard passband BW, standard sampling frequency SW=41.7 kHz, 256 acquisition steps, imaging field of view RC-FOV: 20 cm, and two scans;

B) passband BW which is double the standard passband, sampling frequency BW=83.3 kHz, which is double the standard sampling frequency, 512 acquisition steps, and RO-FOV: 40 cm; and C) passband BW which is triple the standard passband, sampling frequency BW=125 kHz, which is quadruple the standard sampling frequency, 1,024 acquisition steps, and RO-FOV: 80 cm.
<Result>

In the method of this embodiment, as exemplified by FIG. 10C, noise appears at the middle of the image in a read direction RO. The standard deviation is 33.6. The calculated ratio is 2.51. FIG. 10A shows a reconstructed image. FIG. 10B shows a conventional noise spatial distribution. FIG. 10C shows a noise spatial distribution in this embodiment. As is obvious from the conventional noise spatial distribution, the noise level decreases at the middle of the image which is indicated by the arrows. As is obvious from the noise spatial distribution in this embodiment, the noise level is maintained at the middle of the image and decreases at the periphery. FIGS. 11A, 11B, and 11C show noise spatial distributions respectively corresponding to reconstructed images with speed factor SF=1, 2, and 3 which are obtained by parallel imaging. Obviously, spatial noise changes with changes in SF. The image shown in FIG. 11D is a noise spatial distribution with a g factor.
<Speculation>

A noise spatial distribution with little artifact was obtained. The technique of this embodiment was effective for parallel imaging. In this oversampling method, images were separated in the read direction RO and spread in the phase encoding direction. It is obvious that this technique can be used together with parallel imaging in this manner, and data obtained by this technique can accurately reflect the influence of the sensitivity nonuniformity of the coil and that of the g factor at the time of unfolding processing of parallel MRI.

This embodiment can estimate a noise index even in a case in which noise components are not uniform and the influence of the movement of a person as an object cannot be ignored. Since noise is not uniform; the noise can be calculated as a distribution map. That is, even in clinical images, the SNRs of regions of interest, and the CNR between the regions of interest can be estimated more robustly than in the prior art.

(4) First Modification: Phase Correction Processing Accompanying Shift of Sampling Position At the time of resampling (sub-sampling), since the resampling positions of images I1, I2, . . . , differ on the time axis, phase distortion occurs in a frequency domain. Since a standard point corresponds to one rotation in terms of FOV in a real space, ½ distortion (a phase rotation of 180° in terms of FOV) occurs in the case of double SWs. In generally with n-times BWs, 1/n distortion occurs. This phase shift disappears in an absolute-value image. When a complex image, a real part or imaginary part image, or a phase image is to be generated, phase shift correction (to be referred to as phase correction here) is performed.

(5) Second Modification: Case Other than Orthogonal Coordinate System

The single acquisition, two-image difference method (conventional method) in reference 7 is suitable for parallel MRI based on an orthogonal coordinate system. Combining the technique in the present invention with phase correction processing in the read direction described above allows the technique to be applied to the propeller method of rotating a rectangular region R about the origin. When this technique is applied to a radial scan method, phase shift processing is performed as needed (6) Third Modification: Simultaneous Execution of Prevention of Aliasing with respect to Object The following is an example of application of the method of the present invention to an object which is large in size in the read direction (FIG. 11). If a desired FOV is smaller than an object, cutting is generally performed in the read direction by a filter or general oversampling for the prevention of aliasing is performed. In this case, it is important to fold noise, some contrivance is required. If Tp/L0=1.5 where Lp is the size of an object and L0 is an FOV, aliasing can be prevented by 1.25-times oversampling. If, therefore, 3·1.25=3.75 times oversampling is simply performed, a region where the cutoff characteristic is singular can be set as an aliasing region of the image. This can be expressed by 3·(1+((Lp/L0)−1)/2).

As described above, based on imaging conditions, it is possible to change apparent conditions as needed to maintain the characteristic that "noise is folded from the center to the two sides. Positions where frequency characteristics become singular are set at the two ends of an FOV".

Note that the present invention is not limited to the above embodiment, and constituent elements can be variously modified and embodied at the execution stage within the spirit and scope of the invention. Various inventions can be formed by proper combinations of a plurality of constituent elements disclosed in the above embodiments. For example, several constituent elements may be omitted from all the constituent elements in each embodiment. In addition, constituent elements of the different embodiments may be combined as needed.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A magnetic resonance diagnosis apparatus comprising:
a coil assembly including a high-frequency coil;
a transmission unit which excites magnetization of a specific atomic nucleus of an object by driving the high-frequency coil;
a reception unit including a detection unit which receives a magnetic resonance signal via the high-frequency coil, a low-pass filter, and an analog/digital converter;
a control unit which sets a passband of the low-pass filter to not less than three odd multiple of a frequency band determined from an imaging field of view, and sets a sampling frequency of the analog/digital converter to an oversampling frequency exceeding a signal band of the magnetic resonance signal; and
a noise spatial distribution generating unit which generates a noise spatial distribution on the basis of an output from the reception unit.

2. The apparatus according to claim 1, wherein the control unit sets a passband of the low-pass filter to a band three times a frequency band determined from the imaging field of view, and sets a sampling frequency of the analog/digital converter to a frequency two times the signal band.

3. The apparatus according to claim 2, wherein the noise spatial distribution generating unit includes
a resampling processing unit which generates a first resampled data set and a second resampled data set at different resampling positions from data oversampled by the analog/digital converter,
an image reconstruction unit which reconstructs a first image and a second image from the first resampled data set and the second resampled data set respectively, and
a difference processing unit which generates the noise spatial distribution by calculating differences between the first image and the second image.

4. The apparatus according to claim 3, wherein the first image and the second image each is an absolute-value image or a complex image.

5. The apparatus according to claim 1, wherein the control unit sets a passband of the low-pass filter to a band three times a frequency band determined from the imaging field of view, and sets a sampling frequency of the analog/digital converter to a frequency three times the signal band.

6. The apparatus according to claim 5, wherein the noise spatial distribution generating unit includes
a resampling processing unit which generates a first resampled data set, a second resampled data set, and a third resampled data set at different resampling positions from data oversampled by the analog/digital converter,
an image reconstruction unit which reconstructs a first image, a second image, and a third image from the first resampled data set, the second resampled data set, and the third resampled data set respectively, and
a difference processing unit which generates a first noise spatial distribution, a second noise spatial distribution, and a third noise spatial distribution by calculating differences between the first image, the second image, and the third image.

7. The apparatus according to claim 6, wherein the first image, the second image, and the third image each is of an absolute-value image or a complex images.

8. The apparatus according to claim 1, wherein the control unit sets a passband of the low-pass filter to a band three times a frequency band determined from the imaging field of view, and sets a sampling frequency of the analog/digital converter to a frequency four times the signal band.

9. The apparatus according to claim 8, wherein the noise spatial distribution generating unit includes
a resampling processing unit which generates a first resampled data set, a second resampled data set, a third resampled data set, and a fourth resampled data set at different resampling positions from data oversampled by the analog/digital converter,
an image reconstruction unit which reconstructs a first image, a second image, a third image, and a fourth image from the first resampled data set, the second resampled data set, the third resampled data set, and the fourth resampled data respectively, and
a difference processing unit which generates a first noise spatial distribution by calculating differences between the first image and the third image, and a second noise spatial distribution by calculating differences between the second image and the fourth image.

10. The apparatus according to claim 9, wherein the first image, the second image, the third image, and the fourth image each is an absolute-value image or a complex image.

11. The apparatus according to claim 1, wherein the control unit sets a passband of the low-pass filter to a band three times a frequency band determined from the imaging field or view, and sets a sampling frequency of the analog/digital converter to a frequency n times (n is an integer of not less than two) the signal band.

12. The apparatus according to claim 11, wherein the noise spatial distribution generating unit includes
   a resampling processing unit which generates n resampled data sets at different resampling positions from data oversampled by the analog/digital converter,
   an image reconstruction unit which reconstructs n images from the n resampled data sets, and
   a difference processing unit which generates the noise spatial distribution by calculating differences between the n images.

13. The apparatus according to claim 12, wherein the n images each is of an absolute-value image or a complex image.

14. A noise spatial distribution generating method for a magnetic resonance diagnosis apparatus, the method comprising:
   exciting magnetization of a specific atomic nucleus of an object via a high-frequency coil;
   receiving a magnetic resonance signal via the high-frequency coil;
   detecting the received magnetic resonance signal by using a detection unit;
   filtering the detected magnetic resonance signal by using a low-pass filter whose passband is set to not less than three odd multiple of a frequency band determined from an imaging field of view;
   converting the filtered magnetic resonance signal into digital data by using an analog/digital converter whose sampling frequency is set to an oversampling frequency exceeding a signal band of the magnetic resonance signal; and
   generating a noise spatial distribution on the basis of the digital data.

15. A signal acquisition method for a magnetic resonance diagnosis apparatus, the method comprising:
   exciting magnetization of a specific atomic nucleus of an object via a high-frequency coil;
   receiving a magnetic resonance signal via the high-frequency coil;
   detecting the received magnetic resonance signal by using a detection unit;
   filtering the detected magnetic resonance signal by using a low-pass filter whose passband is set to not less than three odd multiple of a frequency band determined from an imaging field of view; and
   converting the filtered magnetic resonance signal into digital data by using an analog/digital converter whose sampling frequency is set to an oversampling frequency exceeding a signal band of the magnetic resonance signal.

* * * * *